(12) United States Patent
Moshe

(10) Patent No.: US 11,622,714 B2
(45) Date of Patent: Apr. 11, 2023

(54) HYPER-SPECTRAL MEMS CHIP ON SMART PHONE FOR CHARACTERIZING LIFE QUALITY OF A LIVING ENTITY VIA IMAGING AND ANALYSIS, AND APPLICATIONS THEREOF

(71) Applicant: Green Vision Systems Ltd., Tel-Aviv (IL)

(72) Inventor: Danny S. Moshe, Tel-Aviv (IL)

(73) Assignee: Green Vision Systems Ltd., Tel-Aviv (IL)

( * ) Notice: Subject to any disclaimer, the term of this patent is extended or adjusted under 35 U.S.C. 154(b) by 1305 days.

(21) Appl. No.: 14/969,033

(22) Filed: Dec. 15, 2015

(65) Prior Publication Data
US 2016/0166196 A1 Jun. 16, 2016

Related U.S. Application Data

(60) Provisional application No. 62/091,961, filed on Dec. 15, 2014.

(51) Int. Cl.
*A61B 5/00* (2006.01)
(52) U.S. Cl.
CPC ............ *A61B 5/486* (2013.01); *A61B 5/0075* (2013.01); *A61B 5/4866* (2013.01);
(Continued)

(58) Field of Classification Search
CPC ........ A61B 5/486; A61B 5/4866; A61B 5/083
See application file for complete search history.

(56) References Cited

U.S. PATENT DOCUMENTS

2007/0038042 A1 2/2007 Freeman et al.
2012/0250025 A1* 10/2012 Moshe .................. B07C 5/3422
356/451
(Continued)

FOREIGN PATENT DOCUMENTS

WO WO 2007/099540 9/2007

OTHER PUBLICATIONS

McMullin Spe. 2014 Advancements in Hyperspectroscopic approaches in food crops.*
(Continued)

*Primary Examiner* — Serkan Akar

(57) ABSTRACT

Methods and apparatuses for characterizing life quality of a living entity via hyper-spectral imaging and analysis, and applications thereof, such as managing life quality of a living entity. Includes acquiring hyper-spectral imaging data and information of: anatomical features of the living entity, and substances consumable by the living entity; generating and maintaining a living entity-specific database containing data and information about the living entity; processing acquired living entity anatomical feature and consumable substance hyper-spectral imaging data and information, and living entity data and information; using processed data and information to generate living entity life quality data and information characteristic of life quality of the living entity. Applicable to any living entity (human, animal, plant). Applicable to integrated microelectromechanical (MEM) [chip level] components in desk top devices or miniature smart/intelligent devices. Applicable to generating, processing, or/and utilizing demographic data and information about living entities and consumable substances.

24 Claims, 5 Drawing Sheets

(52) U.S. Cl.
CPC .......... *A61B 5/6898* (2013.01); *A61B 5/7246* (2013.01); *A61B 5/441* (2013.01); *A61B 5/448* (2013.01); *A61B 5/449* (2013.01); *A61B 2503/40* (2013.01); *A61B 2562/028* (2013.01); *A61B 2576/00* (2013.01)

(56) References Cited

U.S. PATENT DOCUMENTS

| | | | | |
|---|---|---|---|---|
| 2013/0110400 A1* | 5/2013 | Moshe | ................... | G01N 1/26 702/3 |
| 2013/0278631 A1* | 10/2013 | Border | ................ | G02B 27/017 345/633 |
| 2014/0078509 A1* | 3/2014 | Moshe | ................ | G01J 3/0208 356/452 |
| 2018/0296095 A1 | 10/2018 | Moshe | | |

OTHER PUBLICATIONS

NASA Spinoff2010 Hyperspectral imaging.*
Feng et al (Application of Hyperspectral Imaging in Food Safety Inspection and Control: A Review; 2012 Critical Reviews in Food Science and Nutrition). (Year: 2012).*
Bonifazi et al, Hyperspectral imaging applied to complex particulate solids systems, Proc. SPIE 7003, Optical Sensors 2008, 70030F (Apr. 26, 2008).*
Official Action dated Apr. 17, 2017 From the US Patent and Trademark Office Re. U.S. Appl. No. 14/788,950. (22 pages).
Official Action dated Sep. 26, 2017 From the US Patent and Trademark Office Re. U.S. Appl. No. 14/788,950. (17 pages).
Office Action dated Jun. 10, 2019 From the Israel Patent Office Re. Application No. 243112. (9 Pages).
Official Action dated May 6, 2019 From the US Patent and Trademark Office Re. U.S. Appl. No. 14/788,950. (15 pages).

* cited by examiner

Acquiring hyper-spectral imaging data and information of:
    at least one anatomical feature of the living entity, and
    at least one substance consumable by the living entity.

114

Generating and maintaining a living entity-specific database containing data and information about the living entity, via a data-information processing unit.

116      120

Processing the acquired living entity anatomical feature hyper-spectral imaging data and information, the acquired living entity consumable substance hyper-spectral imaging data and information, and the data and information about the living entity, via the data-information processing unit.

118      122

Using the processed data and information, via the data-information processing unit, to generate living entity life quality data and information characteristic of at least one aspect of life quality of the living entity.

130

Using the living entity life quality data and information to assist in managing life quality of the living entity.

Generating a *first level or layer database* of living entity life quality data and information characteristic of at least one aspect of life quality of each living entity of a plurality of living entities.

158

Processing and analyzing the first level or layer database, so as to identify and group together elements thereof having in common at least one attribute or characteristic of the living entity life quality data and information.

162

Generating a *second level or layer database* of a plurality of groups, wherein each group is identifiable according to the at least one common attribute or characteristic of the living entity life quality data and information.

166

Processing and analyzing the second level or layer database of the plurality of groups, for characterizing living entity life quality data and information of the plurality of living entities.

170

Generating a *third level or layer database* of living entity life quality data and information characteristic of the plurality of living entities.

174

Processing and analyzing, and using, the third level or layer database for making predictions about the living entity life quality data and information of the plurality of living entities.

178

Using the predictions about the living entity life quality data and information to assist in managing life quality of the plurality of living entities.

400

HYPER-SPECTRAL MEMS CHIP ON SMART PHONE FOR CHARACTERIZING LIFE QUALITY OF A LIVING ENTITY VIA IMAGING AND ANALYSIS, AND APPLICATIONS THEREOF

RELATED APPLICATION

This application claims the benefit of priority under 35 USC 119(e) of U.S. Provisional Patent Application No. 62/091,961 filed on Dec. 15, 2014, the contents of which are incorporated herein by reference in their entirety.

FIELD OF THE INVENTION

The present invention, in some embodiments thereof, relates to life quality characterization of a living entity, and applications thereof, and more particularly, but not exclusively, to methods and apparatuses for characterizing life quality of a living entity via hyper-spectral imaging and analysis, and applications thereof, such as managing life quality of a living entity. The present invention, in some embodiments thereof, is directed to subject matter corresponding to a unique intersection of the fields and arts relating to: (i) characterizing life quality of a living entity, (ii) managing life quality of a living entity, and (iii) hyper-spectral imaging and analysis. Exemplary embodiments of the present invention are applicable to numerous fields and arts, such as business and health, which involve generating, processing, or/and utilizing demographic data and information about living entities and consumable substances. Exemplary embodiments of the present invention are applicable for being practiced whereby the living entity is any live or living entity, such as a live human being, a live animal, or a live plant.

BACKGROUND OF THE INVENTION

Life quality of a living entity (human, animal, or plant) is associated with/related to a wide variety of numerous different categories of subjects, activities, and data-information about the living entity. Among them are two important categories of: (1) anatomical features of the living entity, and (2) substances consumable by the living entity.

Regarding anatomical features of the living entity, examples are those which are typically exposed and readily viewable to an observer. For example, in the case of the living entity being a live human or live animal, exemplary anatomical features are (partly or fully) exposed skin, hair, or/and nails. For example, in the case of the living entity being a live plant, exemplary anatomical features are (partly or fully) exposed stems, stalks, branches, leaves, or/and flowers.

Regarding substances consumable by the living entity, examples are those substances, materials, or objects, such as food, water, and air, which are typically required and consumed (eaten, ingested, used) by the living entity for maintaining basic good health and life thereof. It is well established and known that characteristics and properties of such exemplary anatomical features of a living entity are (directly or indirectly) affected by characteristics and properties of such exemplary substances, materials, or objects consumable by the living entity.

Accordingly, aspects of life quality of a living entity are (directly or indirectly) associated with/related to, and affected by, characteristics and properties of such exemplary anatomical features of the living entity and of such exemplary substances, materials, or objects consumable by the living entity.

Of potentially wide and general interest, and application, is to have the ability or capability to characterize aspects of life quality of a living entity, where such ability or capability can be used for (directly or indirectly) assisting in managing life quality of the living entity, with an ultimate objective or goal of improving life quality of the living entity.

Hyper-Spectral Imaging and Analysis

Hyper-spectral imaging and analysis has been established as a highly unique, specialized, and sophisticated, combined spectroscopy and imaging type of analytical method or technique, in the more encompassing field or area of analytical science and technology, involving the sciences and technologies of spectroscopy and imaging. By definition, hyper-spectral imaging and analysis is based on a combination of spectroscopy and imaging theories, principles, and practices, which are exploitable for analyzing and classifying various different types and kinds of samples of matter in a highly unique, specialized, and sophisticated, manner.

Hyper-spectral imaging, in general, generating and collecting hyper-spectral images, and, processing and analyzing hyper-spectral image data and information, in particular, theory, principles, and practices thereof, and, related and associated applications and subjects thereof, such as the more general subject of spectral imaging, are well known and taught about in scientific, technical, and patent, literature, and currently practiced in a wide variety of numerous different fields and areas of technology. Exemplary teachings and practices of hyper-spectral imaging and analysis by the same applicant/assignee of the present disclosure are provided in references 1-10 (and references cited therein).

In sharp contrast to the regular or standard spectroscopic imaging technique of 'spectral' imaging and analysis, the more highly specialized, complex, and sophisticated, spectroscopic imaging technique of 'hyper-spectral' imaging and analysis, consists of using a hyper-spectral imaging and analysis system for on-line (real time, near-real time) or off-line generating and collecting (acquiring) hyper-spectral images and spectra (herein, together, generally referred to as hyper-spectral imaging data and information), and, processing and analyzing the acquired hyper-spectral imaging data and information. In hyper-spectral imaging, multiple fields of view of an object (and components thereof) are 'hyper-spectrally' scanned and imaged while the object (and components thereof) is exposed to electromagnetic radiation.

During the hyper-spectral scanning and imaging there is generating and collecting relatively large numbers (up to the order of millions) of multiple spectral (i.e., hyper-spectral) images, 'one-at-a-time', but, in an extremely fast or rapid sequential manner, of the object (and components thereof) emitting electromagnetic radiation at a plurality of many wavelengths (or frequencies, or energies), where the wavelengths (or frequencies, or energies) are associated with different selected (relatively narrow) portions or bands, or bands therein, of an entire hyper-spectrum emitted by the object (and components thereof). A hyper-spectral imaging and analysis system can be operated in an extremely fast or rapid manner for providing exceptionally highly resolved spectral and spatial data and information of an imaged object (and components thereof), with high accuracy and high precision (reproducibility), which are fundamentally unattainable by using a regular or standard spectral imaging and analysis system.

In general, when electromagnetic radiation, for example, in the form of light such as that supplied by the sun, or by a man-made imaging type of illuminating or energy source, such as that used during hyper-spectral imaging, is incident upon an object, the electromagnetic radiation is affected by one or more of the components making up the object, by any combination of electromagnetic radiation absorption, diffusion, reflection, diffraction, scattering, or/and transmission, mechanisms. Moreover, an object whose composition includes organic chemical species or components, ordinarily exhibits some degree or extent of fluorescent or/and phosphorescent properties, characteristics, and behavior, when illuminated by some type of electromagnetic radiation or light, such as ultra-violet (UV), visible (VIS), or infrared (IR), types of light. The affected electromagnetic radiation, in the form of diffused, reflected, diffracted, scattered, or/and transmitted, electromagnetic radiation emitted by, or/and emerging from, the object (and components thereof), is directly and uniquely related to, and can be correlated with, the physical, chemical, or/and biological properties, characteristics, and behavior, of the object, in general, and of the components making up the object, in particular, and therefore represents a spectral ('fingerprint' or 'signature') pattern type of identification and characterization of the object, which is directly applicable for analyzing and classifying the object.

Accordingly, hyper-spectral images generated by, and collected from, an object (and components thereof) are correlated with emission spectra of the object (and components thereof), where the emission spectra correspond to spectral representations in the form of spectral 'fingerprint' or 'signature' pattern types of identification and characterization, of the hyper-spectrally imaged object (and components thereof). Such hyper-spectral image data and information are processed and analyzed by using automatic pattern recognition (APR) or/and optical character recognition (OCR) types of hyper-spectral imaging data and information processing and analysis, for identifying, characterizing, or/and classifying, the physical, chemical, or/and biological properties, characteristics, and behavior, of the hyper-spectrally imaged object (or/and components thereof).

SUMMARY OF THE INVENTION

The present invention, in some embodiments thereof, relates to methods and apparatuses for characterizing life quality of a living entity via hyper-spectral imaging and analysis, and applications thereof, such as managing life quality of a living entity. Exemplary embodiments of the present invention are applicable for being practiced whereby the living entity is any live or living entity, such as a live human being, a live animal, or a live plant. Exemplary embodiments of the present invention are applicable for being practiced whereby the substance consumable by the living entity (consumable substance) is essentially any substance, material, or object, which is consumable or usable (i.e., may be consumed or used) by a living entity in a manner where the consumable substance, material, or object, contacts (touches, comes into direct contact with, or is ingested by) at least part of the body of the living entity.

Exemplary embodiments of the present invention are applicable for being implemented according to different 'temporal' manners or modes of operation, in the context of 'time', including, for example, according to chronological or sequential, periodic, non-periodic, real-time or/and non-real-time manners or modes of operation.

Exemplary embodiments of the present invention are applicable for being implemented according to different 'spatial' manners or modes of operation, particularly, in the context of various different possible 'equipment or hardware' configurations and operations thereof. For example, in the form of a 'standard sized' multi-assembly or multi-device type of an apparatus or system, where one or more of the various assemblies or devices is/are configured and sized, for example, similar to, or on the order of, configurations and sizes of travel baggage (luggage) cases, brief cases, or attaché cases. For example, in the form of a 'miniature sized' multi-assembly or multi-device type of an apparatus or system, where one or more of the various assemblies or devices is/are configured and sized, for example, similar to, or on the order of, configurations and sizes of (integrated) microelectromechanical (MEM) [chip level] components. For example, where one or more of such miniature sized assemblies or devices, or even the entire apparatus or system, is/are configured and operative as part of (inside of) any one of various different types or kinds of a miniature or hand held smart or intelligent device, such as a smart or intelligent phone, a smart or intelligent wallet, a smart or intelligent watch, a smart or intelligent hand bracelet, or a smart or intelligent finger ring, among other possible miniature or hand held smart or intelligent devices, used by people.

Exemplary embodiments of the invention may be implemented by using various different forms of differently configured and sized hyper-spectral imaging terminal or scanner type devices. Such exemplary devices are desk top (hyper-spectral imaging) terminal type devices, or, miniature or hand held (hyper-spectral imaging) scanner type devices. Such exemplary hyper-spectral imaging devices are, for example, in wired or/and wireless electronic communication with any one or more different types or kinds of computing devices. In exemplary embodiments, exemplary computing devices are selected from the group consisting of desk top computing devices, personal (PC) type computing devices, lap top computing devices, and tablet type computing devices, among other types of variously configured and sized computing devices.

Exemplary embodiments of the present invention are applicable for being implemented via local based wired or/and wireless communication methods, protocols, and equipment, or/and via web/internet/cloud based wired or/and wireless communication methods, protocols, and equipment.

According to an aspect of some embodiments of the present invention there is provided a method for characterizing life quality of a living entity via hyper-spectral imaging and analysis, the method comprising: acquiring hyper-spectral imaging data and information of: at least one anatomical feature of the living entity, and at least one substance consumable by the living entity; generating and maintaining a living entity-specific database containing data and information about the living entity, via a data-information processing unit; processing the acquired living entity anatomical feature hyper-spectral imaging data and information, the acquired living entity consumable substance hyper-spectral imaging data and information, and the data and information about the living entity, via the data-information processing unit; and using the processed data and information to generate living entity life quality data and information characteristic of at least one aspect of life quality of the living entity.

According to some embodiments of the invention, the acquiring, the generating and maintaining, the processing, and the using, are performed according to a chronological sequence or plurality of a number of times, spanning a pre-determined period or length of time.

According to some embodiments of the invention, the pre-determined period or length of time is on order of minutes, hours, days, weeks, months, or years.

According to some embodiments of the invention, the acquiring, the generating and maintaining, the processing, and the using, are performed according to a real-time manner or mode of operation, a non-real-time manner or mode of operation, or a combination thereof.

According to some embodiments of the invention, the acquiring, the generating and maintaining, the processing, and the using, are performed in a form of integrated microelectromechanical (MEM) [chip level] components as part of a miniature or hand held smart or intelligent device.

According to some embodiments of the invention, the miniature or hand held smart or intelligent device is selected from the group consisting of smart or intelligent phones, smart or intelligent wallets, smart or intelligent watches, smart or intelligent hand bracelets, and smart or intelligent finger rings.

According to some embodiments of the invention, the processing includes forming sets and databases of interferogram images from the acquired living entity anatomical feature hyper-spectral imaging data and information, the acquired living entity consumable object hyper-spectral imaging data and information, and the data and information about the living entity.

According to some embodiments of the invention, the processing includes segmenting, via analyzing and classifying, as a function of time: (i) elements of the acquired living entity anatomical feature hyper-spectral imaging data and information, (ii) elements of the acquired living entity consumable object hyper-spectral imaging data and information, and (iii) elements of the living entity-specific database containing reference data and information about the living entity.

According to some embodiments of the invention, the using includes correlating at least two of: (i) the segmented acquired living entity anatomical feature hyper-spectral imaging data and information, (ii) the segmented acquired living entity consumable object hyper-spectral imaging data and information, and (iii) the segmented reference data and information about the living entity.

According to some embodiments of the invention, following the correlating, at least some elements of the processed data and information of the acquired living entity anatomical feature hyper-spectral imaging data and information, the acquired living entity consumable object hyper-spectral imaging data and information, and the data and information about the living entity, are fed back to the generating and maintaining, so as to update or/and modify the generating and maintaining the living entity-specific database containing data and information about the living entity.

According to some embodiments of the invention, following the correlating, at least some elements of the generated living entity life quality data and information characteristic of at least one aspect of life quality of the living entity are fed back to the processing, so as to update or/and modify the processing of the acquired living entity anatomical feature hyper-spectral imaging data and information, the acquired living entity consumable object hyper-spectral imaging data and information, and the data and information about the living entity.

According to some embodiments of the invention, the method further comprises using the living entity life quality data and information characteristic of at least one aspect of life quality of the living entity to assist in managing life quality of the living entity.

According to some embodiments of the invention, the acquiring, generating and maintaining, processing, and using, are performed for each living entity of a plurality of living entities, to thereby generate a first level or layer database comprising living entity life quality data and information characteristic of at least one aspect of life quality of the each living entity of the plurality of living entities.

According to some embodiments of the invention, the method further comprises processing and analyzing the first level or layer database, so as to identify and group together elements thereof having in common at least one attribute or characteristic of the living entity life quality data and information.

According to some embodiments of the invention, the attribute or characteristic comprises demographic type data and information of the plurality of living entities, wherein the at least one common attribute or characteristics is associated with common demographic type data and information among the plurality of living entities.

According to some embodiments of the invention, the demographic type data and information is selected from the group consisting of home living places of the living entities, work places of the living entities, travel places of the living entities, and hobbies of the living entities.

According to some embodiments of the invention, the demographic type data and information is selected from the group consisting of sexes of the living entities, ages of the living entities, weights of the living entities, heights of the living entities, skin colors of the living entities, eye colors of the living entities, and hair colors of the living entities.

According to some embodiments of the invention, the demographic type data and information is selected from the group consisting of anatomical features of the living entities.

According to some embodiments of the invention, the attribute or characteristic comprises consumer type data and information of the plurality of living entities, wherein the at least one common attribute or characteristics is associated with common consumer type data and information among the plurality of living entities.

According to some embodiments of the invention, the consumer type data and information is selected from the group consisting of substances consumable by the living entities.

According to some embodiments of the invention, the substances consumable by the living entities are selected from the group consisting of foods and food products, water and water products, air, clothing, bedding, toiletries and bathroom products, cosmetics and cosmetic products, pharmaceuticals and pharmaceutical products, and, medicines and medicine or medicinal products.

According to some embodiments of the invention, the method further comprises generating a second level or layer database comprising a plurality of groups, wherein each group is identifiable according to the at least one common attribute or characteristic of the living entity life quality data and information.

According to some embodiments of the invention, the method further comprises processing and analyzing the second level or layer database of the plurality of groups, for characterizing living entity life quality data and information of the plurality of living entities.

According to some embodiments of the invention, processing and analyzing the second level or layer database includes cross referencing and correlating elements of the second level or layer database containing data and information of the plurality of groups.

According to some embodiments of the invention, the method further comprises generating a third level or layer database comprising living entity life quality data and information characteristic of the plurality of living entities.

According to some embodiments of the invention, the method further comprises processing and analyzing, and using, the third level or layer database for making predictions about the living entity life quality data and information of the plurality of living entities.

According to some embodiments of the invention, the method further comprises using the predictions about the living entity life quality data and information of the plurality of living entities to assist in managing life quality of one or more of each living entity of the plurality of living entities.

According to another aspect of some embodiments of the present invention, there is provided a method for assisting in managing life quality of a living entity via hyper-spectral imaging and analysis, the method comprising: characterizing life quality of the living entity via hyper-spectral imaging and analysis, so as to generate living entity life quality data and information characteristic of at least one aspect of life quality of the living entity; and using the living entity life quality data and information to assist in the managing of life quality of the living entity.

According to some embodiments of the invention, characterizing life quality of the living entity is performed according to the above summarized method.

According to another aspect of some embodiments of the present invention, there is provided an apparatus for characterizing life quality of a living entity via hyper-spectral imaging and analysis, the apparatus comprising: a hyper-spectral imaging unit, configured to acquire hyper-spectral imaging data and information of: at least one anatomical feature of the living entity, and at least one substance consumable by the living entity; a living entity-specific database containing data and information about the living entity; a data-information processing unit, configured to: process the acquired living entity anatomical feature hyper-spectral imaging data and information, the acquired living entity consumable substance hyper-spectral imaging data and information, and the data and information about the living entity; and generate living entity life quality data and information characteristic of at least one aspect of life quality of the living entity.

According to some embodiments of the invention, the hyper-spectral imaging unit, and the data-information processing unit are configured to operate according to a chronological sequence or plurality of a number of times, spanning a pre-determined period or length of time.

According to some embodiments of the invention, the pre-determined period or length of time is on order of minutes, hours, days, weeks, months, or years.

According to some embodiments of the invention, the hyper-spectral imaging unit, the living entity-specific database, and the data-information processing unit are configured to operate according to a real-time manner or mode of operation, a non-real-time manner or mode of operation, or a combination thereof.

According to some embodiments of the invention, the hyper-spectral imaging unit, the living entity-specific database, and the data-information processing unit are configured in a form of integrated microelectromechanical (MEM) [chip level] components as part of a miniature or hand held smart or intelligent device.

According to some embodiments of the invention, the miniature or hand held smart or intelligent device is selected from the group consisting of smart or intelligent phones, smart or intelligent wallets, smart or intelligent watches, smart or intelligent hand bracelets, and smart or intelligent finger rings.

According to some embodiments of the invention, the data-information processing unit is configured to process the data and information by forming sets and databases of interferogram images from the acquired living entity anatomical feature hyper-spectral imaging data and information, the acquired living entity consumable object hyper-spectral imaging data and information, and the data and information about the living entity.

According to some embodiments of the invention, the data-information processing unit is configured to process the data and information by segmenting, as a function of time: (i) elements of the acquired living entity anatomical feature hyper-spectral imaging data and information, (ii) elements of the acquired living entity consumable object hyper-spectral imaging data and information, and (iii) elements of the living entity-specific database containing reference data and information about the living entity.

According to some embodiments of the invention, the data-information processing unit is further configured to correlate at least two of: (i) the segmented acquired living entity anatomical feature hyper-spectral imaging data and information, (ii) the segmented acquired living entity consumable object hyper-spectral imaging data and information, and (iii) the segmented reference data and information about the living entity.

According to some embodiments of the invention, the data-information processing unit is configured to update or/and modify at least some elements of the processed data and information of the acquired living entity anatomical feature hyper-spectral imaging data and information, the acquired living entity consumable object hyper-spectral imaging data and information, and the data and information about the living entity.

According to some embodiments of the invention, the apparatus further comprises a controller-processor configured to control the hyper-spectral imaging unit.

According to some embodiments of the invention, the controller-processor is operatively connected to the hyper-spectral imaging unit and to the data-information processing unit.

According to some embodiments of the invention, the data and information about the living entity is transferrable between the living entity-specific database and the data-information processing unit.

According to some embodiments of the invention, the data-information processing unit is configured to feed back the processed data and information to the living entity-specific database.

According to some embodiments of the invention, the living entity life quality data and information is fed back to the data-information processing unit.

According to some embodiments of the invention, data and information, or/and control signals, are transferrable between the data-information processing unit and the hyper-spectral imaging unit.

According to some embodiments of the invention, data and information, or/and control signals, are transferrable between the controller-processor and the hyper-spectral imaging unit.

According to some embodiments of the invention, data and information, or/and control signals, are transferrable between the data-information processing unit and the controller-processor.

According to some embodiments of the invention, the data-information processing unit is configured to enable using the living entity life quality data and information to assist in managing life quality of the living entity.

According to some embodiments of the invention, a plurality of hyper-spectral imaging units, and a plurality of data-information processing units, are configured to operate for a corresponding plurality of living entities, to thereby generate a first level or layer database comprising living entity life quality data and information characteristic of at least one aspect of life quality of each living entity of the plurality of living entities.

According to some embodiments of the invention, the plurality of data-information processing units is operatively connected to a central or global data-information processing unit configured to process and analyze the first level or layer database, so as to identify and group together elements thereof having in common at least one attribute or characteristic of the living entity life quality data and information.

According to some embodiments of the invention, the central or global data-information processing unit is configured to generate a second level or layer database comprising a plurality of groups, wherein each group is identifiable according to the at least one common attribute or characteristic of the living entity life quality data and information.

According to some embodiments of the invention, the central or global data-information processing unit is configured to process and analyze the second level or layer database of the plurality of groups, for characterizing living entity life quality data and information of the plurality of living entities.

According to some embodiments of the invention, the central or global data-information processing unit is configured to process and analyze the second level or layer database includes cross referencing and correlating elements of the second level or layer database containing data and information of the plurality of groups.

According to some embodiments of the invention, the central or global data-information processing unit is configured to generate a third level or layer database comprising living entity life quality data and information characteristic of the plurality of living entities.

According to some embodiments of the invention, the central or global data-information processing unit is configured to process and analyze, and use, the third level or layer database for making predictions about the living entity life quality data and information of the plurality of living entities.

According to some embodiments of the invention, the predictions are used to assist in managing life quality of one or more of each living entity of the plurality of living entities.

According to another aspect of some embodiments of the present invention, there is provided an apparatus for assisting in managing life quality of a living entity via hyper-spectral imaging and analysis, the apparatus comprising: an apparatus for characterizing life quality of the living entity via hyper-spectral imaging and analysis, configured to generate living entity life quality data and information characteristic of at least one aspect of life quality of the living entity; and a data-information processing unit, configured to enable using the living entity life quality data and information to assist in the managing of life quality of the living entity.

According to some embodiments of the invention, the apparatus for characterizing life quality of the living entity via hyper-spectral imaging and analysis includes the same exemplary components, functionalities, and features, which are included in the preceding summarized apparatus.

All technical and/or scientific words, terms, or/and phrases, used herein throughout the present disclosure have the same or similar meaning as commonly understood by one of ordinary skill in the art to which the invention pertains, unless otherwise specifically defined or stated herein. Although materials or/and methods equivalent or similar to those described herein can be used in practicing or/and testing embodiments of the invention, exemplary materials or/and methods are described below. In case of conflict, the patent specification, including definitions, will control. In addition, materials, methods, and examples described herein are illustrative only and are not intended to be necessarily limiting.

Implementation of some embodiments of the invention can involve performing or completing selected tasks manually, automatically, or a combination thereof. Moreover, according to actual instrumentation and equipment of some embodiments of the invention, several selected tasks could be implemented by hardware, by software, firmware, or a combination thereof, using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the present invention are herein described, by way of example only, with reference to the accompanying drawings. With specific reference now to the drawings in detail, it is stressed that the particulars shown are by way of example and for purposes of illustrative description of some embodiments of the present invention. In this regard, the description taken together with the accompanying drawings make apparent to those skilled in the art how some embodiments of the present invention may be practiced.

In the drawings:

FIG. 1 is a flow diagram of an exemplary method for characterizing life quality of a living entity via hyper-spectral imaging and analysis, and applications thereof, in accordance with some embodiments of the invention;

FIG. 3 is a flow diagram of additional exemplary steps (procedures) of the exemplary method for characterizing life quality of a living entity via hyper-spectral imaging and analysis presented in FIG. 1, highlighting exemplary implementation according to multi-level/multi-layer manner or mode of operation, in accordance with some embodiments of the invention;

DESCRIPTION OF SPECIFIC EMBODIMENTS OF THE INVENTION

Figure 2:
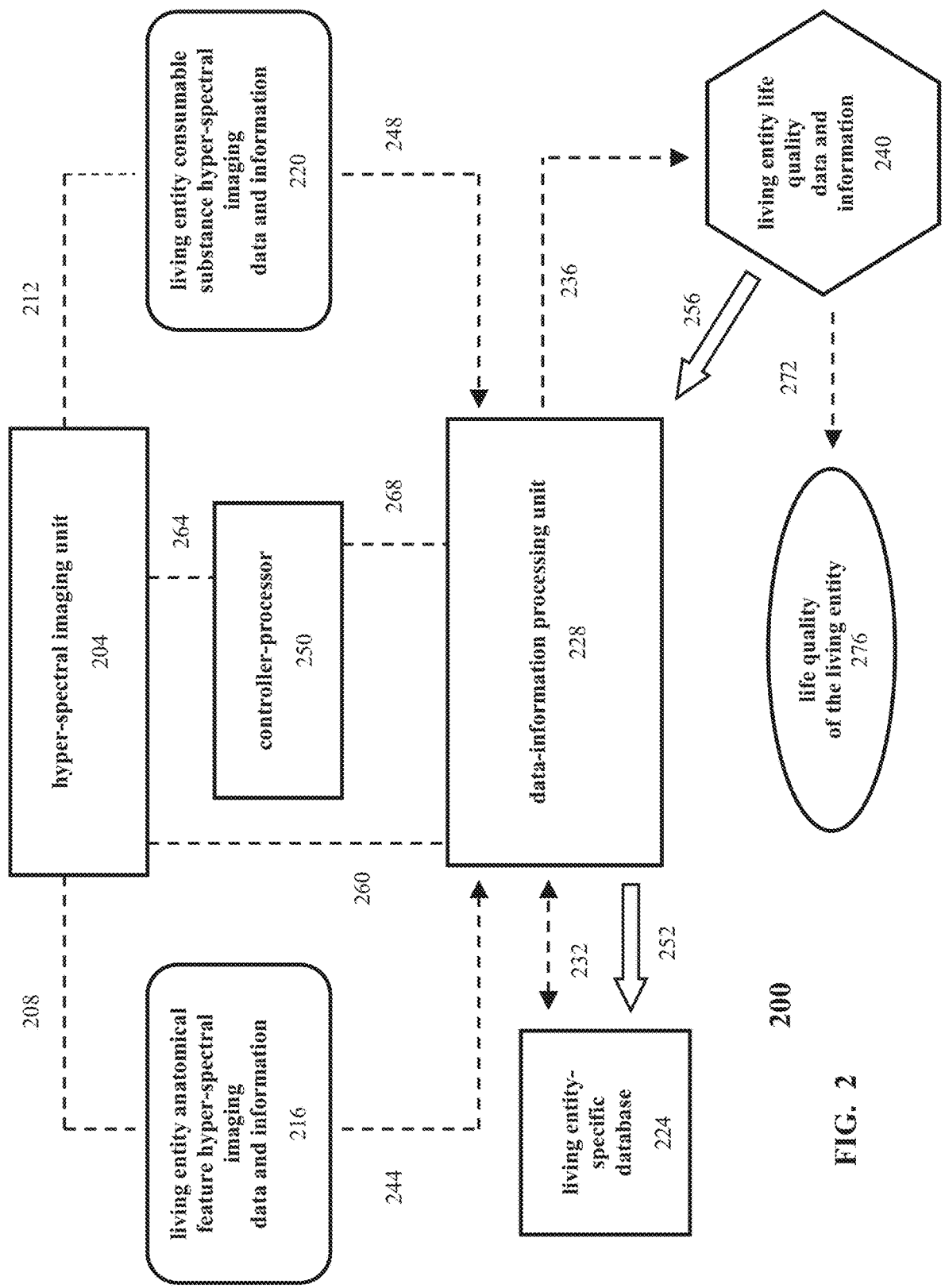
FIG. 2 is a (block-type) schematic diagram of an exemplary apparatus for characterizing life quality of a living entity via hyper-spectral imaging and analysis, and applications thereof, in accordance with some embodiments of the invention.

The present invention, in some embodiments thereof, relates to life quality characterization of a living entity, and applications thereof, and more particularly, but not exclusively, to methods and apparatuses for characterizing life quality of a living entity via hyper-spectral imaging and analysis, and applications thereof, such as managing life quality of a living entity. The present invention, in some embodiments thereof, is directed to subject matter corresponding to a unique intersection of the fields and arts relating to: (i) characterizing life quality of a living entity, (ii) managing life quality of a living entity, and (iii) hyper-spectral imaging and analysis. Exemplary embodiments of the present invention are applicable to numerous fields and arts, such as business and health, which involve generating, processing, or/and utilizing demographic data and information about living entities and consumable substances.

Exemplary embodiments of the invention are applicable for being practiced whereby the living entity is any live or living entity, such as a live human being, a live animal, or a live plant. Exemplary embodiments of the invention are applicable for being practiced whereby the substance consumable by the living entity (consumable substance) is essentially any substance, material, or object, which is consumable or usable (i.e., may be consumed or used) by a living entity in a manner where the consumable substance, material, or object, contacts (touches, comes into direct contact with, or is ingested by) at least part of the body of the living entity.

Exemplary embodiments of the invention are applicable for being implemented according to different 'temporal' manners or modes of operation, in the context of 'time', including, for example, according to chronological or sequential, periodic, non-periodic, real-time or/and non-real-time manners or modes of operation.

Exemplary embodiments of the invention are applicable for being implemented according to different 'spatial' manners or modes of operation, particularly, in the context of various different possible 'equipment or hardware' configurations and operations thereof. For example, in the form of a 'standard sized' multi-assembly or multi-device type of an apparatus or system, where one or more of the various assemblies or devices is/are configured and sized, for example, similar to, or on the order of, configurations and sizes of travel baggage (luggage) cases, brief cases, or attaché cases. For example, in the form of a 'miniature sized' multi-assembly or multi-device type of an apparatus or system, where one or more of the various assemblies or devices is/are configured and sized, for example, similar to, or on the order of, configurations and sizes of (integrated) microelectromechanical (MEM) [chip level] components. For example, where one or more of such miniature sized assemblies or devices, or even the entire apparatus or system, is/are configured and operative as part of (inside of) any one or more of various different types or kinds of a miniature or hand held smart or intelligent device, such as a smart or intelligent phone, a smart or intelligent wallet, a smart or intelligent watch, a smart or intelligent hand bracelet, or a smart or intelligent finger ring, among other possible miniature or hand held smart or intelligent devices, used by people.

Exemplary embodiments of the invention may be implemented by using various different forms of differently configured and sized hyper-spectral imaging terminal or scanner type devices. Such exemplary devices are desk top (hyper-spectral imaging) terminal type devices, or, miniature or hand held (hyper-spectral imaging) scanner type devices. Such exemplary hyper-spectral imaging devices are, for example, in wired or/and wireless electronic communication with any one or more different types or kinds of computing devices. In exemplary embodiments, exemplary computing devices are selected from the group consisting of desk top computing devices, personal (PC) type computing devices, lap top computing devices, and tablet type computing devices, among other types of variously configured and sized computing devices.

Exemplary embodiments of the invention are applicable for being implemented via local based wired or/and wireless communication methods, protocols, and equipment, or/and via web/internet/cloud based wired or/and wireless communication methods, protocols, and equipment.

In the following illustrative description of some embodiments of the invention, reference is made to the figures (FIGS. 1 through 5). Throughout the following description and accompanying drawings, same reference numbers refer to same components, elements, or features. It is to be understood that the invention is not necessarily limited in its application to the details of construction and the arrangement of the components and/or methods set forth in the following illustrative description. The invention is capable of other embodiments or of being practiced or carried out in various ways.

Additionally, it is to be fully understood that certain aspects, characteristics, and features, of the present invention, which are illustratively described and presented in the context or format of a plurality of separate embodiments, may also be illustratively described and presented in any suitable combination or sub-combination in the context or format of a single embodiment. Conversely, various aspects, characteristics, and features, of the present invention, which are illustratively described and presented in combination or sub-combination in the context or format of a single embodiment, may also be illustratively described and presented in the context or format of a plurality of separate embodiments.

For example, the following includes illustrative description of several aspects of some embodiments of the invention. Specifically, the following presentation includes illustrative description of some embodiments of a method for characterizing life quality of a living entity via hyperspectral imaging and analysis, and some embodiments of an apparatus (in the form of a system or of a small device) for characterizing life quality of a living entity via hyperspectral imaging and analysis. It is to be understood that some embodiments of the disclosed method may be implemented independent of the disclosed apparatus, or by using some embodiments of the disclosed apparatus, and vice versa. Accordingly, it is to be understood that illustrative description of one or more particular aspects of some embodiments of the invention may be considered independent or dependent of the respective illustrative description of one or more particular aspects of some other embodiments of the invention.

Living (Live) Entities

The phrase 'living entity', as used herein, refers to any living (live) entity, such as a living (live) human being, a living (live) animal, or, a living (live) plant. The phrase 'living entity', as used herein, is synonymous with, and equivalent to, the phrase 'live entity'.

The living entity can be of any age, from a newly (new) born or formed living entity, to an old or aged living entity.

For example, the living entity may be a live human being, for example, selected from the group consisting of a newly (new) born baby (infant), a baby (infant), a child, an adolescent, a young adult, an adult, a middle aged person, and an old-aged (elderly) person.

For example, the living entity may be a live animal member of the animal kingdom (phylum, class, order, family, genus, or species thereof), of any age.

For example, the living entity may be a live plant member of the plant kingdom (phylum/division, class, order, family, genus, or species thereof), of any age.

Anatomical Features/Body Parts

The phrase 'anatomical feature', as used herein, refers to essentially any anatomical feature, or part of the body, of a living entity which is or can be (partly or fully) exposed and at least partly viewable by an observer, either with or without movement or manipulation of the body of the living entity or/and removal of something covering the body of the living entity. The phrase 'anatomical feature', as used herein, may be considered synonymous with, and equivalent to, the phrases 'part of the body' and 'body part', unless specifically stated otherwise.

In the case of the living entity being a living human or living animal, exemplary anatomical features are those parts of the human or animal body which are typically (partly or fully) exposed and at least partly viewable by an observer, such as skin, hair, nails, teeth. Additional exemplary anatomical features of a living human or living animal are those body parts associated with an eye, such as an eyelid, an eyebrow, and an eyelash.

In the case of the living entity being a living plant, exemplary anatomical features are those parts of the plant body which are typically (partly or entirely) exposed and at least partly viewable by an observer, such as stems, stalks, branches, leaves, flowers, or/and roots.

Consumable Substances, Materials, Objects

The phrase 'substance consumable by the living entity', or, alternatively, the phrase 'consumable substance', as used herein, refers to essentially any substance, material, or object, which is consumable or usable (i.e., may be consumed or used) by a living entity in a manner where the consumable substance, material, or object, contacts (touches, comes into direct contact with, or is ingested by) at least part of the body of the living entity.

The phrases 'substance consumable' and 'consumable substance' are herein used in a synonymous and equivalent manner, and it is to be understood that appearance and meaning of either of these phrases are equivalent to appearance and meaning of the other phrase. Moreover, the phrases 'substance consumable' and 'consumable substance', as used herein, are synonymous with, and equivalent to, the phrases 'material consumable', 'consumable material', 'object consumable', and 'consumable object', unless specifically stated otherwise. Accordingly, it is to be understood that appearance and meaning of any of these phrases are equivalent to appearance and meaning of the other phrases, unless specifically stated otherwise.

Exemplary consumable substances, materials, or objects, are those which are typically required and consumed by a living entity for regularly (daily) maintaining basic good health, well being, and quality of life thereof. Additional exemplary consumable substances, materials, or objects, are those which are consumed by a living entity for maintaining, or/and improving, or/and enhancing, or/and treating, health, well being, and quality of life thereof.

Such exemplary consumable substances, materials, or objects, are selected from the group consisting of foods (food products), water (water products), air, clothing, bedding, toiletries (bathroom products), cosmetics (cosmetic products), and pharmaceuticals (pharmaceutical products)/medicines (medicine [medicinal] products).

Additional exemplary consumable substances, materials, or objects, are those which are typically not required by a living entity for regularly (daily) maintaining basic good health, well being, and quality of life thereof, but, are consumed by the living entity. Such exemplary consumable substances, materials, or objects, are selected from the group consisting of tobacco (and tobacco products), alcohol (and alcohol products), and drugs (and drug products).

Here, such drugs (and drug products), although possibly made up of, or including, same or similar components or/and ingredients making up, or included in, above stated pharmaceuticals (pharmaceutical products)/medicines (medicine [medicinal] products), are typically not required by a living entity for regularly (daily) maintaining basic good health, well being, and quality of life thereof, but, are nevertheless consumed by the living entity. Such consumption may be, for example, in the context of drug abuse. Accordingly, such drugs (and drug products) are consumed by a living entity for purposes other than for routinely maintaining, or/and improving, or/and enhancing, or/and treating, health, well being, and quality of life thereof.

Foods/Food Products

Exemplary (consumable) foods (food products) are essentially any food item or product which are obtainable and consumable (edible, fit to be eaten, ingestible, fit to be ingested). Such exemplary (consumable) foods (food products) are consumable in their natural states, or consumable (edible, ingestible) after processing (cleaning, cutting, spicing, cooking, baking, roasting, etc.). Exemplary (consumable) foods (food products) are essentially any food item or product which is derived from one or more naturally existing agricultural products. Exemplary (consumable) foods (food products) are essentially any food item or product which is partly or wholly synthetically made or manufactured.

Examples of the above stated types or kinds of exemplary (consumable) foods (food products) are selected from the group consisting of grains or seeds (and grain or seed products), fruits (and fruit products), vegetables (and vegetable products), fish (and fish products), meat (and meat products), and dairy products.

Any of the above listed or described exemplary (consumable) foods (food products) may be in essentially any physicochemical form of a solid, or a liquid, or a combination thereof.

Any of the above listed or described exemplary (consumable) foods (food products) may be suitable for use in essentially any type or kind of human, veterinary, or agricultural/botanical, application.

Water/Water Products

Exemplary (consumable) water (water products) are essentially any water-based liquid which is consumable (ingestible, fit to be ingested). Exemplary (consumable) water (water products) are tap (faucet) water, filtered water, bottled water, water-based beverages, and water-based drinks. Such exemplary (consumable) water (water products) are obtainable and consumable (ingestible) in their natural states, or consumable (ingestible) after processing (cleaning, filtering, removing or adding minerals, etc.).

Any of the above listed or described exemplary (consumable) water (water products) may be suitable for use in essentially any type or kind of human, veterinary, or agricultural/botanical, application.

Air

Exemplary (consumable) air is outdoor air, or indoor air present inside of a residential building (dwelling), such as a home or apartment, or air inside of a commercial (office) building, and which comes into contact with a living entity. Exemplary (consumable) air is air that is processed, re-processed, circulated, or/and generated, by an air processing device, such as an air filtration device, or an air conditioner. Such air typically contains dust and other air particular matter, among other substances, materials, and objects, possibly present in the (consumable) air.

Any of the above listed or described food (food products), water (water products), air, types of consumable substances, materials, or objects, may include essentially any type or kind, and amount, of contamination (contaminant, pollutant, impurity, or the like). Examples of such contamination are human growth products, animal growth products, plant growth products, fertilizers, pesticides, insecticides, herbicides, and the like.

Clothing/Garments

Exemplary (consumable) clothing (garments) are essentially any type or kind of outer wear clothing (garments), or under wear clothing (garments).

Any of the above listed or described exemplary (consumable) clothing (garments) may be suitable for use in essentially any type or kind of human or veterinary application.

Bedding/Bedclothes

Exemplary (consumable) bedding (bedclothes) are sheets, blankets, and other coverings of a bed, such as pillow cases, that are ordinarily used with a bed for a living entity to sleep.

Any of the above listed or described exemplary (consumable) bedding (bedclothes) may be suitable for use in essentially any type or kind of human or veterinary application.

Toiletries/Bathroom Products

Exemplary (consumable) toiletries/bathroom products are soaps, soap products, and related soap type body cleaning products, shampoos, hair conditioners, and related hair cleaning/conditioning type products, toothpaste, mouth wash and related mouth cleaning type products, toothbrushes and related mouth cleaning type products, hair combs, hair brushes, body towels, hand towels, toilet paper, wash cloths, tissues, deodorants, and antiperspirants.

Any of the above listed or described exemplary (consumable) toiletries/bathroom products may be in essentially any physicochemical form of a solid, or a liquid, or a combination thereof.

Any of the above listed or described exemplary (consumable) toiletries/bathroom products may be suitable for use in essentially any type or kind of human or veterinary application.

Cosmetics/Cosmetic Products

Exemplary (consumable) cosmetics (cosmetic products) are facial makeup, and body/skin/facial/leg/hand powders, ointments, creams, lotions, gels, oils. Additional exemplary (consumable) cosmetics (cosmetic products) are formulations (sunscreens, sun blockers, and the like) applied to prevent or minimize UV radiation from damaging the skin.

Any of the above listed exemplary (consumable) cosmetics (cosmetic products) may be in essentially any physicochemical form of a solid, or a liquid, or a combination thereof.

Any of the above listed or described exemplary (consumable) cosmetics (cosmetic products) may be suitable for use in essentially any type or kind of human or veterinary application.

Pharmaceuticals/Pharmaceutical Products/Medicines/Medicine (Medicinal) Products

Exemplary (consumable) pharmaceuticals (pharmaceutical products)/medicines (medicine [medicinal] products) are essentially any over-the-counter, or prescription only, type pharmaceutical (pharmaceutical product)/medicine (medicine [medicinal] product) which is consumed by a living entity for maintaining, or/and improving, or/and enhancing, or/and treating, health, well being, and quality of life thereof.

Any of the above listed or described exemplary (consumable) pharmaceuticals (pharmaceutical products)/medicines (medicine [medicinal] products) may be in essentially any physicochemical form of a solid, a semi-solid, a liquid, or a combination thereof. Any of the above listed or described exemplary (consumable) pharmaceuticals (pharmaceutical products)/medicines (medicine [medicinal] products) may be suitable for use in essentially any type or kind of human or veterinary application.

Real-Time Manner or Mode of Implementation

The term 'real-time', as used herein, refers to essentially any aspect of the disclosed method, or any aspect of the disclosed apparatus, which is (automatically or/and manually) performed, implemented, or used, at the same time, or at nearly the same time, with negligible or insignificant time lag, that a targeted (observed, tracked, monitored) event, scene, or situation of interest occurs or takes place. For example, the term 'real-time', as used herein, refers to essentially any action, activity, step, procedure, process, operation, function, or piece of equipment, of the disclosed method or apparatus, which is (automatically or/and manually) performed, implemented, or used, at the same time, or at nearly the same time, with negligible or insignificant time lag, that a targeted (monitored, tracked, observed) event, scene, or situation of interest occurs or takes place.

Steps or procedures, sub-steps or sub-procedures, and, equipment and materials, system units, system sub-units, devices, assemblies, sub-assemblies, mechanisms, structures, components, elements, and configurations, and, peripheral equipment, utilities, accessories, and materials, as well as operation and implementation, of exemplary embodiments, alternative embodiments, specific configurations, and, additional and optional aspects, characteristics, or features, thereof, of some embodiments of the present invention, are better understood with reference to the following illustrative description and accompanying drawings. Throughout the following illustrative description and accompanying drawings, same reference notation and terminology (i.e., numbers, letters, symbols, terms, and phrases) are consistently used and refer to same steps or procedures, sub-steps or sub-procedures, system units, system sub-units, devices, assemblies, sub-assemblies, mechanisms, structures, components, elements, and configurations, and, peripheral equipment, utilities, accessories, materials, components, elements, or/and parameters.

An aspect of some embodiments of the present invention is a method for characterizing life quality of a living entity via hyper-spectral imaging and analysis.

Referring now to the drawings, FIG. 1 is a flow diagram of an exemplary embodiment of the method (generally, indicated as, and referred to by, reference number 100), including the indicated exemplary steps (procedures) and features thereof, for characterizing life quality of a living entity via hyper-spectral imaging and analysis, and applications thereof. In FIG. 1, exemplary steps (procedures) of the exemplary embodiment shown are enclosed inside separate blocks (frames) which are assigned reference numbers, and are also indicated by dashed line arrows with accompanying reference numbers drawn between other exemplary steps. Accordingly, as shown, exemplary steps (procedures) are enclosed inside of blocks (frames) 112, 114, 116, 118, and 130, and indicated by dashed line curved arrows with accompanying reference numbers 122 and 120. As shown in FIG. 1, the exemplary embodiment of the method 100 includes the following exemplary steps (procedures) and features.

In exemplary step (procedure) referenced by 112, there is acquiring hyper-spectral imaging data and information of: at least one anatomical feature of the living entity, and at least one substance, material, or object consumable by the living entity.

In exemplary step (procedure) referenced by 114, there is generating and maintaining a living entity-specific database containing data and information about the living entity, via a data-information processing unit.

In exemplary step (procedure) referenced by 116, there is processing the acquired living entity anatomical feature hyper-spectral imaging data and information, the acquired living entity consumable object hyper-spectral imaging data and information, and the data and information about the living entity, via the data-information processing unit.

In exemplary step (procedure) referenced by 118, there is using the processed data and information, via the data-information processing unit, to generate living entity life quality data and information characteristic of at least one aspect of life quality of the living entity.

In exemplary, optional, step (procedure) referenced by 120, the processed data and information of the acquired living entity anatomical feature hyper-spectral imaging data and information, the acquired living entity consumable object hyper-spectral imaging data and information, and the data and information about the living entity, obtained via exemplary step 116, are fed back to the preceding step (procedure) 114, for example, as a way of updating or/and modifying step (procedure) 114 of generating and maintaining a living entity-specific database containing data and information about the living entity.

In exemplary, optional, step (procedure) referenced by 122, the living entity life quality data and information characteristic of at least one aspect of life quality of the living entity (generated via exemplary step 118) are fed back to the preceding step (procedure) 116, for example, as a way of updating or/and modifying step (procedure) 116 of processing the data-information.

Exemplary embodiments of method 100, optionally, further includes exemplary step (procedure) referenced by 130, of using the living entity life quality data and information to assist in managing life quality of the living entity. This exemplary step (procedure) may be considered as part of an exemplary application of some embodiments of the method 100.

Accordingly, another aspect of some embodiments of the present invention is a method for assisting in managing life quality of a living entity via hyper-spectral imaging and analysis, the method including the exemplary steps (procedures) and features of: characterizing life quality of the living entity via hyper-spectral imaging and analysis, so as to generate living entity life quality data and information characteristic of at least one aspect of life quality of the living entity; and using the living entity life quality data and information to assist in the managing of life quality of the living entity.

In exemplary embodiments of such a method, the step (procedure) of characterizing life quality of the living entity is performed according to the preceding described exemplary embodiments of the method 100, as shown in FIG. 1, including exemplary steps (procedures) 112, 114, 116, 118, 130, 122, and 120.

Another aspect of some embodiments of the present invention is an apparatus for characterizing life quality of a living entity via hyper-spectral imaging and analysis, and applications thereof.

FIG. 2 is a (block-type) schematic diagram of an exemplary embodiment of an apparatus (generally, indicated as, and referred to by, reference number 200), including exemplary components, functionalities, and features thereof, for characterizing life quality of a living entity via hyper-spectral imaging and analysis, and applications thereof. The exemplary embodiment of the apparatus 200 is, in a non-limiting manner, particularly suitable for implementing the exemplary embodiment of the method 100 presented in FIG. 1. Similarly, the exemplary embodiment of the method 100 presented in FIG. 1, is, in a non-limiting manner, suitable for implementing the exemplary embodiment of the apparatus 200 shown in FIG. 2.

As shown in FIG. 2, the exemplary embodiment of the apparatus 200 includes the following exemplary components, functionalities, and features thereof.

A hyper-spectral imaging unit 204, configured to acquire (indicated by dashed arrows 208 and 212) hyper-spectral imaging data and information of: at least one anatomical feature of the living entity 216, and at least one object consumable by the living entity 220.

A living entity-specific database 224 containing data and information about the living entity.

A data-information processing unit 228, operatively connected to the hyper-spectral imaging unit and configured to: generate and maintain (indicated by two-headed dashed arrow 232) the living entity-specific database 224; to process the acquired living entity anatomical feature hyper-spectral imaging data and information 216, the acquired living entity consumable object hyper-spectral imaging data and information 220, and the data and information about the living entity contained in the living entity-specific database 224; and using the processed data and information to generate (indicated by dashed arrow 236) living entity life quality data and information 240 characteristic of at least one aspect of life quality of the living entity.

In exemplary embodiments, apparatus 200 additionally includes a controller-processor 250 configured to control processes and operation of the hyper-spectral imaging unit 204.

In exemplary embodiments, acquired living entity anatomical feature hyper-spectral imaging data and information 216 is transferred (indicated by dashed arrow 244) from hyper-spectral imaging unit 204 to data-information processing unit 228, and acquired living entity consumable object hyper-spectral imaging data and information 220 is transferred (indicated by dashed arrow 248) from hyper-spectral imaging unit 204 to data-information processing unit 228.

In exemplary embodiments, data and information about the living entity contained in the living entity-specific database 224 is transferrable (indicated by dashed two-headed arrow 232) between living entity-specific database 224 and data-information processing unit 228. In exemplary, optional, embodiments, data-information processing unit 228 feeds back (indicated by hollow arrow 252) processed data and information to living entity-specific database 224, for example, as a way of updating or/and modifying the living entity-specific database 224 and the data and information about the living entity contained therein.

In exemplary embodiments, living entity life quality data and information 236 is fed back (indicated by hollow arrow 256) to data-information processing unit 228, for example, as a way of data-information processing unit 228 updating or/and modifying processing of the living entity life quality data and information 240.

In exemplary embodiments, data and information, or/and control signals, are transferrable (indicated by dashed line 260) between data-information processing unit 228 and hyper-spectral imaging unit 204. In exemplary embodiments, data and information, or/and control signals, are transferrable (indicated by dashed line 264) between controller-processor 250 and hyper-spectral imaging unit 204. In exemplary embodiments, data and information, or/and control signals, are transferrable (indicated by dashed line 268) between data-information processing unit 228 and controller-processor 250.

In exemplary embodiments of apparatus 200, the data-information processing unit 228 is optionally configured to enable using (indicated by dashed arrow 272) the living entity life quality data and information 240 to assist in managing life quality of the living entity 276. This exemplary optional configuration may be considered as part of an exemplary application of apparatus 200.

Accordingly, another aspect of some embodiments of the present invention is an apparatus for assisting in managing life quality of a living entity via hyper-spectral imaging and analysis, the apparatus includes the following exemplary components, functionalities, and features thereof: an apparatus for characterizing life quality of the living entity via hyper-spectral imaging and analysis, configured to generate living entity life quality data and information characteristic of at least one aspect of life quality of the living entity; and a data-information processing unit, configured to enable using the living entity life quality data and information to assist in the managing of life quality of the living entity.

In exemplary embodiments of such an apparatus, the apparatus for characterizing life quality of the living entity via hyper-spectral imaging and analysis includes the same exemplary components, functionalities, and features, which are included in the preceding described exemplary embodiments of apparatus 200, as shown in FIG. 2.

Temporal Aspects, Characteristics, and Features

Exemplary embodiments of the present invention are applicable for being implemented according to different 'temporal' manners or modes of operation, in the context of 'time'.

As a function of time, for example, wherein embodiments of the invention are implemented a number of times, for example, according to a chronological sequence or plurality of a number of times, spanning a pre-determined period or length of time, wherein an exemplary pre-determined period or length of time is on the order of minutes, hours, days, weeks, months, or years.

Accordingly, in exemplary embodiments, exemplary method 100, and exemplary steps (procedures) thereof, for characterizing life quality of a living entity via hyper-spectral imaging and analysis, are performed as a function of time. For example, wherein exemplary method 100, and exemplary steps (procedures) thereof, are performed a number of times, for example, according to a chronological sequence or plurality of a number of times, spanning a pre-determined period or length of time.

Accordingly, in exemplary embodiments, exemplary apparatus 200, and, exemplary components and functionalities thereof, for characterizing life quality of a living entity via hyper-spectral imaging and analysis, are configured to operate as a function of time. For example, wherein exemplary apparatus 200, and, exemplary components and functionalities thereof, are configured to operate a number of times, for example, according to a chronological sequence or plurality of a number of times, spanning a pre-determined period or interval of time.

In exemplary embodiments, an exemplary pre-determined period or length of time is on the order of minutes, hours, days, weeks, months, or years.

Exemplary embodiments of exemplary method 100, or/and of exemplary apparatus 200, are implemented in a manner corresponding to chronologically and sequentially, periodically or/and non-periodically characterizing life quality of the living entity via hyper-spectral imaging and analysis. Such a mode of implementation corresponds to chronologically and sequentially, periodically or/and non-periodically observing, tracking, or monitoring, the living entity life quality data and information 240 characteristic of at least one aspect of life quality of the living entity.

Exemplary embodiments of exemplary method 100, or/and of exemplary apparatus 200, are implemented according to a real-time manner or mode of operation, or/and according to a non-real-time manner or mode of operation.

According to a real-time manner or mode of operation, for example, wherein exemplary method 100, and exemplary steps (procedures) thereof, are performed according to a real-time manner or mode of operation. For example, wherein exemplary apparatus 200, and, exemplary components and functionalities thereof, are configured to operate according to a real-time manner or mode. For example, wherein at least one action, activity, step, procedure, process, operation, function, or piece of equipment, of the exemplary method 100 or of the exemplary apparatus 200, is (automatically or/and manually) performed, implemented, or used, at the same time, or at nearly the same time, with negligible or insignificant time lag, that a targeted (monitored, tracked, observed) event, scene, or situation of interest occurs or takes place, in the context of characterizing life quality of a living entity via hyper-spectral imaging and analysis.

According to a non-real-time manner or mode of operation, for example, wherein exemplary method 100, and exemplary steps (procedures) thereof, are performed according to a non-real-time manner or mode of operation. For example, wherein exemplary apparatus 200, and, exemplary components and functionalities thereof, are configured to operate according to a non-real-time manner or mode. For example, wherein at least one action, activity, step, procedure, process, operation, function, or piece of equipment, of the exemplary method 100 or of the exemplary apparatus 200, is (automatically or/and manually) performed, implemented, or used, not at the same time, but with significant time lag, that a targeted (monitored, tracked, observed) event, scene, or situation of interest occurs or takes place, in the context of characterizing life quality of a living entity via hyper-spectral imaging and analysis.

Spatial Aspects, Characteristics, and Features

Exemplary embodiments of the present invention are applicable for being implemented according to different 'spatial' manners or modes of operation, particularly, in the context of various different possible 'equipment or hardware' configurations and operations thereof.

For example, in the form of a 'standard sized' multi-assembly or multi-device type of an apparatus or system, where one or more of the various assemblies or devices is/are configured and sized, for example, similar to, or on the order of, configurations and sizes of travel baggage (luggage) cases, brief cases, or attaché cases.

For example, in the form of a 'miniature sized' multi-assembly or multi-device type of an apparatus or system, where one or more of the various assemblies or devices is/are configured and sized, for example, similar to, or on the order of, configurations and sizes of (integrated) microelectromechanical (MEM) [chip level] components. For example, where one or more of such miniature sized assemblies or devices, or even the entire apparatus or system, is/are configured and operative as part of (inside of) any one of various different types or kinds of a miniature or hand held smart or intelligent device, such as a smart or intelligent phone, a smart or intelligent wallet, a smart or intelligent watch, a smart or intelligent hand bracelet, or a smart or intelligent finger ring, among other possible miniature or hand held smart or intelligent devices, used by people.

Accordingly, for example, in exemplary embodiments, exemplary method 100, and exemplary steps (procedures) thereof, and exemplary apparatus 200, and, exemplary components and functionalities thereof, for characterizing life quality of a living entity via hyper-spectral imaging and analysis, are implemented in the form of a 'standard sized' multi-assembly or multi-device type of an apparatus or system, where one or more of the various assemblies or devices is/are configured and sized, for example, similar to, or on the order of, configurations and sizes of travel baggage (luggage) cases, brief cases, or attaché cases.

Figure 4:
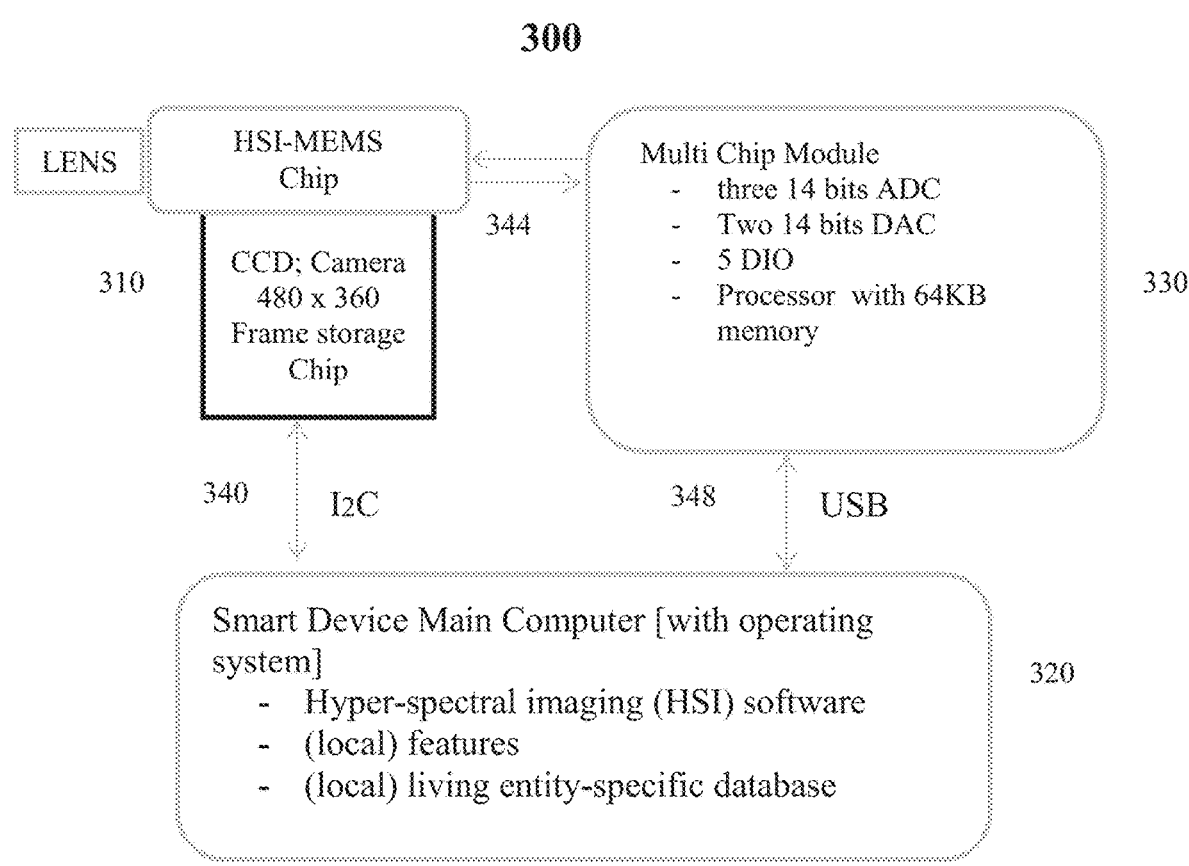
FIG. 4 is a (block-type) schematic diagram of an exemplary apparatus for characterizing life quality of a living entity via hyper-spectral imaging and analysis, and applications thereof, highlighting an exemplary 'chip level' type design and construction, configurable and operable with integrated microelectromechanical (MEM) [chip level] components as part of (inside of) an exemplary miniature smart or intelligent device, in accordance with some embodiments of the invention.
Figure 5:
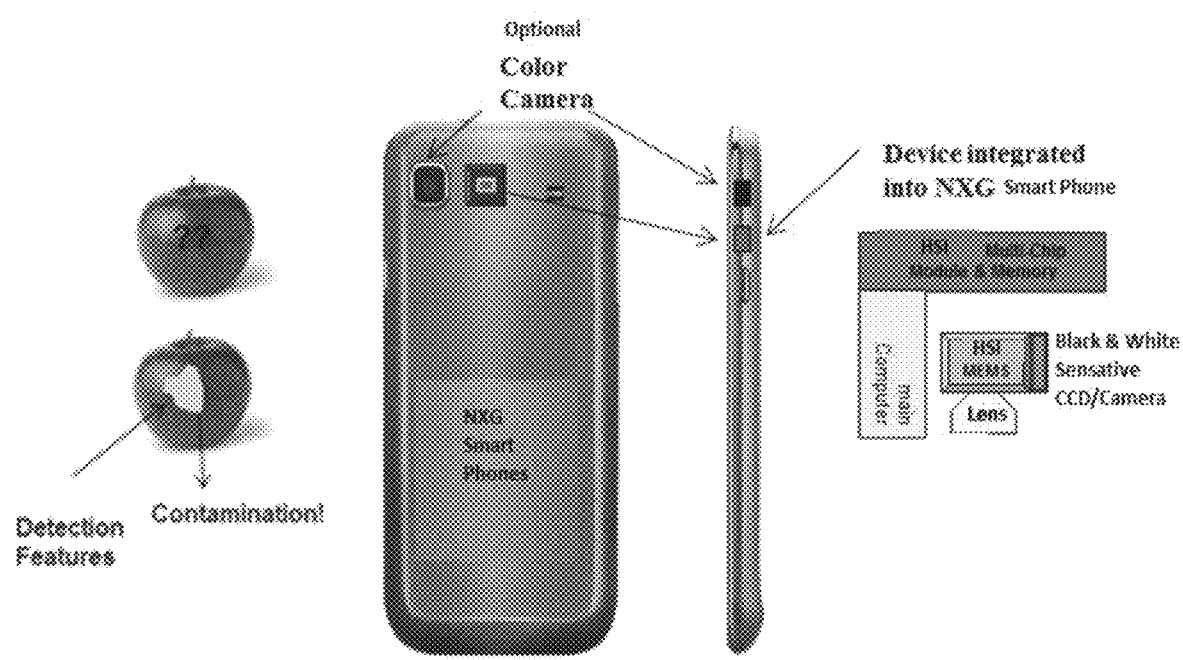
FIG. 5 is a schematic diagram illustrating an exemplary apparatus for characterizing life quality of a living entity via hyper-spectral imaging and analysis, and applications thereof, as an example of the apparatus of FIG. 4, configured into an exemplary smart phone, in accordance with some embodiments of the invention.

Accordingly, for example, in exemplary embodiments, exemplary method 100, and exemplary steps (procedures) thereof, and exemplary apparatus 200, and, exemplary components and functionalities thereof, for characterizing life quality of a living entity via hyper-spectral imaging and analysis, are implemented in the form of a 'miniature sized' multi-assembly or multi-device type of an apparatus or system, where one or more of the various assemblies or devices is/are configured and sized, for example, similar to, or on the order of, configurations and sizes of (integrated) microelectromechanical (MEM) [chip level] components. For example, where one or more of such miniature sized assemblies or devices, or even the entire apparatus or system, is/are configured and operative as part of (inside of) any one of various different types or kinds of a miniature or hand held smart or intelligent device (for example, as shown in FIG. 4), such as a smart or intelligent phone (for example, as shown in FIG. 5), a smart or intelligent wallet, a smart or intelligent watch, a smart or intelligent hand bracelet, or a smart or intelligent finger ring, among other possible miniature or hand held smart or intelligent devices, used by people.

Exemplary embodiments of the invention (for example, exemplary method 100, or/and exemplary apparatus 200) may be implemented by using various different forms of differently configured and sized hyper-spectral imaging terminal or scanner type devices. Such exemplary devices are desk top (hyper-spectral imaging) terminal type devices, or, miniature or hand held (hyper-spectral imaging) scanner type devices. Such exemplary hyper-spectral imaging devices are, for example, in wired or/and wireless electronic communication with any one or more different types or kinds of computing devices. In exemplary embodiments, exemplary computing devices are selected from the group consisting of desk top computing devices, personal (PC) type computing devices, lap top computing devices, and tablet type computing devices, among other types of variously configured and sized computing devices.

Additional Functional (Operational) and Structural Aspects, Characteristics, and Features Exemplary embodiments of the present invention, for example, as illustratively described herein above in the context of exemplary method 100 (FIG. 1) and exemplary apparatus 200 (FIG. 2), for characterizing life quality of a living entity via hyper-spectral imaging and analysis, include the following exemplary additional functional (operational) or/and structural aspects, characteristics, and features.

In exemplary embodiments, for example, via exemplary step (procedure) 112, using, for example, hyper-spectral imaging unit 204, there is acquiring hyper-spectral imaging data and information of at least one anatomical feature of the living entity, and acquiring hyper-spectral imaging data and information of at least one substance consumable by the living entity.

In exemplary embodiments, the living entity may be any living (live) entity, such as a living (live) human being, a living (live) animal, or, a living (live) plant, for example, as listed and described hereinabove.

In exemplary embodiments, the at least one anatomical feature of the living entity may be essentially any anatomical feature, or part of the body, of the living entity which is or can be (partly or fully) exposed and at least partly viewable by an observer, either with or without movement or manipulation of the body of the living entity or/and removal of something covering the body of the living entity, for example, as listed and described hereinabove. In exemplary embodiments, the at least one substance consumable by the living entity may be essentially any substance, material, or object, which is consumable or usable (i.e., may be consumed or used) by a living entity in a manner where the consumable substance, material, or object, contacts (touches, comes into direct contact with, or is ingested by) at least part of the body of the living entity, for example, as listed and described hereinabove.

In exemplary embodiments, for example, via exemplary step (procedure) 114, via data-information processing unit 228, there is generating and maintaining a living entity-specific database containing data and information about the living entity.

In exemplary embodiments, the living entity-specific database contains data and information including hyper-spectral imaging data and information about the hereinabove listed and described anatomical features of the living entity, and, also contains data and information including hyper-spectral data and information about the hereinabove listed and described substances consumable by the living entity. Such a living entity-specific database serves as an updatable 'reference' type of database containing reference data and information, including reference hyper-spectral data and information, about the living entity.

In exemplary embodiments, for example, via exemplary step (procedure) 116, and via the data-information processing unit 228, there is processing the acquired living entity anatomical feature hyper-spectral imaging data and information, the acquired living entity consumable object hyper-spectral imaging data and information, and the data and information about the living entity.

In exemplary embodiments, such processing includes performing at least some of the following exemplary steps (procedures), via the data-information processing unit.

Forming sets and databases of interferogram images from the acquired living entity anatomical feature hyper-spectral imaging data and information, the acquired living entity consumable object hyper-spectral imaging data and information, and the data and information about the living entity.

Segmenting (via analyzing and classifying), for example, as a function of time: (i) elements of the acquired living entity anatomical feature hyper-spectral imaging data and information, (ii) elements of the acquired living entity consumable object hyper-spectral imaging data and information, and (iii) elements of the living entity-specific database containing the (reference) data and information about the living entity.

Such segmenting, for example, as a function of time, is done in order to generate or form: (i) segmented (analyzed and classified) acquired living entity anatomical feature hyper-spectral imaging data and information, (ii) segmented (analyzed and classified) acquired living entity consumable object hyper-spectral imaging data and information, and (iii) segmented (analyzed and classified) reference data and information about the living entity, as a function of time.

In exemplary embodiments, following the preceding segmenting, for example, via exemplary step (procedure) 118, and via the data-information processing unit 228, there is using the processed data and information to generate living entity life quality data and information characteristic of at least one aspect of life quality of the living entity.

This step includes, for example, correlating (via using software programs based on, for example, fuzzy logic decision making, and matching/mismatching, algorithms) at least two of: (i) the (time dependent) segmented (analyzed and classified) acquired living entity anatomical feature hyper-spectral imaging data and information, (ii) the (time dependent) segmented (analyzed and classified) acquired living entity consumable object hyper-spectral imaging data and information, and (iii) the (time dependent) segmented (analyzed and classified) reference data and information about the living entity.

Such correlating, for example, as a function of time, is done in order to generate the living entity life quality data and information characteristic of at least one aspect of life quality of the living entity, for example, as a function of time.

In exemplary embodiments, for example, following the preceding correlating, for example, via exemplary step (procedure) 120, at least some elements of the processed data and information of the acquired living entity anatomical feature hyper-spectral imaging data and information, the acquired living entity consumable object hyper-spectral imaging data and information, and the data and information about the living entity, obtained via exemplary step 116, are fed back to the preceding step (procedure) 114, for example, as a way of updating or/and modifying step (procedure) 114 of generating and maintaining the living entity-specific database containing data and information about the living entity.

In exemplary embodiments, for example, following the preceding correlating, for example, via exemplary step (procedure) 122, at least some elements of the generated living entity life quality data and information characteristic of at least one aspect of life quality of the living entity are fed back to the preceding step (procedure) 116, for example, as a way of updating or/and modifying step (procedure) 116 of processing the acquired living entity anatomical feature hyper-spectral imaging data and information, the acquired living entity consumable object hyper-spectral imaging data and information, and the data and information about the living entity.

In exemplary embodiments, for example, via exemplary step (procedure) 130, the living entity life quality data and information is used to assist in managing life quality of the living entity. This exemplary step (procedure) may be considered as part of an exemplary application of some embodiments of the present invention.

Multi-Level/Multi-Layer Manner or Mode of Implementation

Exemplary embodiments of the present invention, for example, as illustratively described herein above in the context of exemplary method 100 (FIG. 1) and exemplary apparatus 200 (FIG. 2), for characterizing life quality of a living entity via hyper-spectral imaging and analysis, and applications thereof, may be implemented according to a multi-level or multi-layer mode or manner of operation.

Such a multi-level or multi-layer mode or manner of operation corresponds to extending implementation of exemplary method 100 (FIG. 1) and exemplary apparatus 200 (FIG. 2), for characterizing life quality of a living entity via hyper-spectral imaging and analysis, and applications thereof, to a plurality of individual living entities using a corresponding plurality of individual apparatuses 200 (FIG. 2). Accordingly, in exemplary embodiments, each individual living entity separately uses another one of the plurality of apparatuses 200 for generating its own living entity life quality data and information 240 characteristic of at least one aspect of life quality of that individual living entity. From this living entity life quality data and information, there is generating a first level or layer database which includes living entity life quality data and information characteristic of at least one aspect of life quality of each individual living entity of the plurality of living entities. The first level or layer database is then processed and analyzed, for generating a second level or layer database which includes a plurality of groups, wherein each group is identifiable according to at least one common attribute or characteristic of the living entity life quality data and information of the plurality of living entities. The second level or layer database is then processed and analyzed, for generating a third level or layer database which includes grouped living entity life quality data and information characteristic of different groups of the plurality of living entities.

The third level or layer database is then processed and analyzed, and used, for making predictions about the living entity life quality data and information of the plurality of living entities, at the level of a plurality of different groups of living entities, or/and at the level of a single group of living entities, or/and at the level of an individual living entity. Such predictions about the living entity life quality data and information of the plurality of living entities are then used to assist in managing life quality of one or more of each living entity of the plurality of living entities, for example, at the level of a plurality of different groups of living entities, or/and at the level of a single group of living entities, or/and at the level of an individual living entity.

FIG. 3 is a flow diagram of additional exemplary steps (procedures) [generally, indicated as, and referred to by, reference number 150], of the exemplary method 100 for characterizing life quality of a living entity via hyper-spectral imaging and analysis presented in FIG. 1, highlighting exemplary implementation according to multi-level/multi-layer manner or mode of operation.

In exemplary step (procedure) 154, there is generating a first level or layer database which includes living entity life quality data and information characteristic of at least one aspect of life quality of each living entity of the plurality of living entities. In exemplary embodiments of the method, for example, method 100 (FIG. 1), the steps (procedures) of acquiring (112), generating and maintaining (114), processing (116), and using (118), are performed for each living entity of a plurality of living entities, to thereby generate the first level or layer database including living entity life quality data and information characteristic of at least one aspect of life quality of each living entity of the plurality of living entities.

Exemplary step (procedure) 154 is performed, for example, via a plurality of living entities using a corresponding plurality of apparatuses 200 (FIG. 2), where, for example, each individual living entity separately uses another one of the plurality of apparatuses 200 for generating its own living entity life quality data and information 240 characteristic of at least one aspect of life quality of that individual living entity. Exemplary step (procedure) 154 is performed, for example, via a plurality of individual or local data-information processing units 228 operatively connected to a central or global data-information processing unit.

In exemplary step (procedure) 158, there is processing and analyzing the first level or layer database, for example, via the central or global data-information processing unit, so as to identify and group together elements thereof having in common at least one attribute or characteristic of the living entity life quality data and information.

In exemplary embodiments, the attribute or characteristic comprises demographic type data and information of the plurality of living entities, wherein the at least one common attribute or characteristics is associated with common demographic type data and information among the plurality of living entities. In exemplary embodiments, the demographic type data and information is selected from the group consisting of home living places of the living entities, work places of the living entities, travel places of the living entities, and hobbies of the living entities. In exemplary embodiments, the demographic type data and information is selected from the group consisting of sexes of the living entities, ages of the living entities, weights of the living entities, heights of the living entities, skin colors of the living entities, eye colors of the living entities, and hair colors of the living entities.

In exemplary embodiments, the demographic type data and information is selected from the group consisting of anatomical features of the living entities. In exemplary embodiments, the attribute or characteristic includes consumer type data and information of the plurality of living entities, wherein the at least one common attribute or characteristics is associated with common consumer type data and information among the plurality of living entities. In exemplary embodiments, the consumer type data and information is selected from the group consisting of substances consumable by the living entities. In exemplary embodiments, the substances consumable by the living entities are selected from the group consisting of foods and food products, water and water products, air, clothing, bedding, toiletries and bathroom products, cosmetics and cosmetic products, pharmaceuticals and pharmaceutical products, and, medicines and medicine or medicinal products.

In exemplary step (procedure) 162, there is generating, for example, via the central or global data-information processing unit, a second level or layer database which includes a plurality of groups, wherein each group is identifiable according to the at least one common attribute or characteristic of the living entity life quality data and information.

In exemplary step (procedure) 166, there is processing and analyzing, for example, via the central or global data-information processing unit, the second level or layer database of the plurality of groups, for characterizing living entity life quality data and information of the plurality of living entities. In exemplary embodiments, processing and analyzing the second level or layer database includes cross referencing and correlating elements of the second level or layer database containing data and information of the plurality of groups.

In exemplary step (procedure) 170, there is generating, for example, via the central or global data-information processing unit, a third level or layer database which includes living entity life quality data and information characteristic of the plurality of living entities.

In exemplary step (procedure) 174, there is processing and analyzing, and using, for example, via the central or global data-information processing unit, the third level or layer database for making predictions about the living entity life quality data and information of the plurality of living entities.

In exemplary step (procedure) 178, there is using the predictions about the living entity life quality data and information of the plurality of living entities to assist in managing life quality of one or more of each living entity of the plurality of living entities.

The above described multi-level or multi-layer mode or manner of operation, in the context of exemplary method 100, is implemented, for example, by using a corresponding plurality of apparatuses 200 (FIG. 2), where, for example, each individual living entity separately uses another one of the plurality of apparatuses 200. According to such implementation, a plurality of hyper-spectral imaging units 204 and a corresponding plurality of data-information processing units 228 are configured to operate for a corresponding plurality of living entities, to thereby generate the first level or layer database including the living entity life quality data and information characteristic of at least one aspect of life quality of each living entity of the plurality of living entities. In exemplary embodiments, a plurality of individual or local data-information processing units 228 is operatively connected to a central or global data-information processing unit.

In exemplary embodiments, the central or global data-information processing unit is configured to process and analyze the first level or layer database, so as to identify and group together elements thereof having in common at least one attribute or characteristic of the living entity life quality data and information. In exemplary embodiments, the central or global data-information processing unit is further configured to generate the second level or layer database including a plurality of groups, wherein each group is identifiable according to at least one common attribute or characteristic of the living entity life quality data and information. In exemplary embodiments, the central or global data-information processing unit is further configured to process and analyze the second level or layer database of the plurality of groups, for characterizing living entity life quality data and information of the plurality of living entities. In exemplary embodiments, the central or global data-information processing unit is configured to process and analyze the second level or layer database by cross referencing and correlating elements of the second level or layer database containing data and information of the plurality of groups.

In exemplary embodiments, central or global data-information processing unit is configured to generate the third level or layer database including living entity life quality data and information characteristic of the plurality of living entities. In exemplary embodiments, central or global data-information processing unit is configured to process and analyze, and use, the third level or layer database for making predictions about the living entity life quality data and information of the plurality of living entities. In exemplary embodiments, the predictions are used to assist in managing life quality of one or more of each living entity of the plurality of living entities.

Exemplary Applications

As described hereinabove, exemplary embodiments of the present invention are applicable for being implemented according to different 'spatial' manners or modes of operation, particularly, in the context of 'equipment or hardware' configurations and operations thereof. Such exemplary embodiments may be, for example, in the form of a 'miniature sized' multi-assembly or multi-device type of an apparatus or system, where one or more of the various assemblies or devices is/are configured and sized, for example, similar to, or on the order of, configurations and sizes of (integrated) microelectromechanical (MEM) [chip level] components.

FIG. 4 is a (block-type) schematic diagram of an exemplary apparatus (generally, indicated as, and referred to by, reference number 300) for characterizing life quality of a living entity via hyper-spectral imaging and analysis, and applications thereof, highlighting an exemplary 'chip level' type design and construction, configurable and operable with integrated microelectromechanical (MEM) [chip level] components as part of (inside of) an exemplary miniature smart or intelligent device.

As shown in FIG. 4, exemplary apparatus 300 includes the following exemplary components.

A hyper-spectral imaging unit 310, configured to acquire hyper-spectral imaging data and information of: at least one anatomical feature of a living entity, and at least one object consumable by the living entity. Hyper-spectral imaging unit 310 includes an HSI-MEMS chip, a CCD—camera chip, and a lens assembly. In alternative exemplary embodiments, hyper-spectral imaging unit 310 includes an HSI-MEMS terminal box instead of an HSI-MEMS chip.

A data-information processing unit 320, configured as a smart device main computer including: an operating system, hyper-spectral imaging (HSI) software, (local) features data and information, and a (local) living entity-specific database (for example, 224 of FIG. 2) containing data and information about the living entity.

Data-information processing unit 320 is configured to: process the acquired living entity anatomical feature hyper-spectral imaging data and information (for example, 216 of FIG. 2), the acquired living entity consumable object hyper-spectral imaging data and information (for example, 220 of FIG. 2), and the data and information about the living entity (for example, 224 of FIG. 2).

Data-information processing unit 320 is also configured to generate (for example, 236 of FIG. 2) living entity life quality data and information (for example, 240 of FIG. 2) characteristic of at least one aspect of life quality of the living entity.

In exemplary embodiments of apparatus 300, the data-information processing unit 320 is optionally configured to enable using (for example, 272 of FIG. 2) the living entity life quality data and information (for example, 240 of FIG. 2) to assist in managing life quality of the living entity (for example, 276 of FIG. 2). This exemplary optional configuration may be considered as part of an exemplary application of apparatus 300.

Exemplary apparatus 300 also includes a controller-processor 330 configured to control operation of the hyper-spectral imaging unit 310.

In exemplary embodiments, data and information, or/and control signals, are transferrable (indicated by the term "I2C" and the two-headed arrow 340) between data-information processing unit 320 and hyper-spectral imaging unit 310.

In exemplary embodiments, data and information, or/and control signals, are transferrable (indicated by the pair of arrows 344) between controller-processor 330 and hyper-spectral imaging unit 310.

In exemplary embodiments, data and information, or/and control signals, are transferrable (indicated by the term "USB" and the two-headed arrow 348) between data-information processing unit 320 and controller-processor 330.

FIG. 5 is a schematic diagram illustrating an exemplary apparatus (generally, indicated as, and referred to by, reference number 400) for characterizing life quality of a living entity via hyper-spectral imaging and analysis, and applications thereof, as an example of the apparatus 300 of FIG. 4, configured as part of (inside of) an exemplary smart or intelligent phone.

Each of the following terms written in singular grammatical form: 'a', 'an', and 'the', as used herein, means 'at least one', or 'one or more'. Use of the phrase one or more herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

Each of the phrases 'consisting of' and 'consists of', as used herein, means 'including and limited to'.

The phrase 'consisting essentially of', as used herein, means that the stated entity or item (system, system unit, system sub-unit, device, assembly, sub-assembly, mechanism, structure, component, element, or, peripheral equipment, utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional 'feature or characteristic' being a system unit, system sub-unit, device, assembly, sub-assembly, mechanism, structure, component, or element, or, peripheral equipment, utility, accessory, or material, step or procedure, sub-step or sub-procedure), but only if each such additional 'feature or characteristic' does not materially alter the basic novel and inventive characteristics or special technical features, of the claimed entity or item.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range from 1 to 6' also refers to, and encompasses, all possible sub-ranges, such as from '1 to 3', from '1 to 4', from '1 to 5', from '2 to 4', from '2 to 6', from '3 to 6', etc., and individual numerical values, such as '1', '1.3', '2', '2.8', '3', '3.5', '4', '4.6', '5', '5.2', and '6', within the stated or described numerical range of from '1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

The phrase 'operatively connected', as used herein, equivalently refers to the corresponding synonymous phrases 'operatively joined', and 'operatively attached', where the operative connection, operative joint, or operative attachment, is according to a physical, or/and electrical, or/and electronic, or/and mechanical, or/and electro-mechanical, manner or nature, involving various types and kinds of hardware or/and software equipment and components.

It is to be fully understood that certain aspects, characteristics, and features, of the present invention, which are illustratively described and presented in the context or format of a plurality of separate embodiments, may also be illustratively described and presented in any suitable combination or sub-combination in the context or format of a single embodiment. Conversely, various aspects, characteristics, and features, of the present invention, which are illustratively described and presented in combination or sub-combination in the context or format of a single embodiment, may also be illustratively described and presented in the context or format of a plurality of separate embodiments.

Although the present invention has been illustratively described and presented by way of specific exemplary embodiments thereof, and examples thereof, it is evident that many alternatives, modifications, and variations, thereof, will be apparent to those skilled in the art. Accordingly, it is intended that all such alternatives, modifications, and variations, fall within, and are encompassed by, the scope of the appended claims.

All patents, patent applications, and publications, cited or referred to in this specification are herein incorporated in their entirety by reference into the specification, to the same extent as if each individual patent, patent application, or publication, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

REFERENCES

1. WIPO PCT Pat. Appl. Int'l. Pub. No. WO 2012/150557, published Nov. 8, 2012, of PCT Pat. Appl. No. PCT/IB2012/052195, filed May 2, 2012, of same applicant/assignee as the present disclosure, entitled: "Microelectromechanical System (MEMS) And (MEM) Optical Interferometer For Hyper-Spectral Imaging And Analysis".
2. WIPO PCT Pat. Appl. Intl. Pub. No. WO 2007/0990540, published Sep. 7, 2007, of PCT Pat. Appl. No. PCT/IL2007/000268, filed Mar. 1, 2007, of same applicant/assignee as the present invention, entitled: "Processing And Analyzing Hyper-spectral Image Data And Information Via Dynamic Database Updating".
3. U.S. Pat. No. 8,817,253, to Moshe, of same applicant/assignee as the present invention, entitled: "Hyper-spectral Imaging And Analysis Of A Sample Of Matter, For Identifying And Characterizing An Object Of Interest Therein".
4. U.S. Pat. No. 8,159,661, to Moshe, of same applicant/assignee as the present invention, entitled: "Hyper-spectral Imaging And Analysis Of A Sample Of Matter, And Preparing A Solution Or Suspension Therefrom".

5. U.S. Pat. No. 7,411,682, to Moshe, of same applicant/assignee as the present invention, entitled: "Real Time High Speed High Resolution Hyper-Spectral Imaging".
6. U.S. Pat. No. 6,697,510, to Moshe, of same applicant/assignee as the present invention, entitled: "Method For Generating Intra-particle Crystallographic Parameter Maps And Histograms Of A Chemically Pure Crystalline Particulate Substance".
7. U.S. Pat. No. 6,694,048, to Moshe, of same applicant/assignee as the present invention, entitled: "Method For Generating Intra-particle Morphological Concentration/Density Maps And Histograms Of A Chemically Pure Particulate Substance".
8. U.S. Pat. No. 6,438,261, to Moshe, et al., of same applicant/assignee as the present invention, entitled: "Method Of In-situ Focus-Fusion Multi-layer Spectral Imaging And Analysis".
9. U.S. Pat. No. 6,091,843, to Horesh, et al., of same applicant/assignee as the present invention, entitled: "Method Of Calibration And Real-time Analysis Of Particulates".
10. U.S. Pat. No. 5,880,830, to Schechter, of same applicant/assignee as the present invention, entitled: "Spectral Imaging Method For On-line Analysis Of Polycyclic Aromatic Hydrocarbons In Aerosols".

What is claimed is:

1. A method for characterizing life quality of a living human or animal via hyper-spectral imaging and analysis, the method comprising:
    acquiring hyper-spectral imaging data and information of:
    (a) at least one anatomical feature selected from the group consisting of hair, nails, teeth, eyelid, eyebrow, and eyelash of the living human or animal, and
    (b) at least one substance to be consumed by the living human or animal, wherein said hyper-spectral imaging data and information of at least one consumable substance relates to said at least one consumable substance prior to said consumable substance coming into contact with the living human or animal, and
    wherein said at least one substance comprises at least one substance selected from the group consisting of foods and food products, clothing, bedding, toiletries and bathroom products, cosmetics and cosmetic products, pharmaceuticals and pharmaceutical products, and, medicines and medicine or medicinal products;
    generating and maintaining a living human- or animal-specific database containing (c) reference hyper-spectral imaging data and information about said at least one anatomical feature of the living human or animal and said at least one substance to be consumed, via a data-information processing unit;
    applying fuzzy logic to correlate (a) said acquired living human or animal anatomical feature hyper-spectral imaging data and information, (b) said acquired living human or animal consumable substance hyper-spectral imaging data and information, and (c) said reference hyper-spectral imaging data and information;
    wherein said acquiring, said generating and maintaining, and said correlating are performed according to a chronological sequence, a plurality of times, spanning a pre-determined period or length of time; and
    by said data-information processing unit, generating based on said correlation living human or animal life quality data and information characteristic of at least one aspect of life quality of the living human or animal as a function of time;
    wherein the method comprises obtaining demographic data pertaining to the living human or animal, and wherein said life quality data and information characteristic of at least one aspect of life quality is generated also based on said demographic data; and
    wherein said processing includes segmenting, via analyzing and classifying, as a function of time:
    (i) elements of said acquired living human or animal anatomical feature hyper-spectral imaging data and information,
    (ii) elements of said acquired living human or animal consumable object hyper-spectral imaging data and information, and
    (iii) elements of said living human- or animal-specific database containing reference data and information about the living human or animal,
    wherein said using includes correlating at least two of:
    (i) said segmented acquired living human or animal anatomical feature hyper-spectral imaging data and information,
    (ii) said segmented acquired living human or animal consumable object hyper-spectral imaging data and information, and
    (iii) said segmented reference data and information about the living human or animal,
    wherein said at least two of:
    (i) said segmented acquired living human or animal anatomical feature hyper-spectral imaging data and information,
    (ii) said segmented acquired living human or animal consumable object hyper-spectral imaging data and information, and
    (iii) said segmented reference data and information about the living human or animal
    are correlated based on said fuzzy logic, to generate the living human or animal life quality data and information characteristic of at least one aspect of life quality of the living human or animal as a function of time.

2. The method of claim 1, wherein said pre-determined period or length of time is on order of minutes, hours, days, weeks, months, or years.

3. The method of claim 1, wherein said acquiring, said generating and maintaining, said processing, and said using, are performed according to a real-time manner or mode of operation, a non-real-time manner or mode of operation, or a combination thereof.

4. The method of claim 1, wherein said acquiring, said generating and maintaining, said processing, and said using, are performed in a form of integrated microelectromechanical (MEM) [chip level] components as part of a miniature or hand held smart or intelligent device.

5. The method of claim 4, wherein said miniature or hand held smart or intelligent device is selected from the group consisting of smart or intelligent phones, smart or intelligent wallets, smart or intelligent watches, smart or intelligent hand bracelets, and smart or intelligent finger rings.

6. The method of claim 1, wherein said processing includes forming sets and databases of interferogram images from said acquired living human or animal anatomical feature hyper-spectral imaging data and information, said acquired living human or animal consumable object hyper-spectral imaging data and information, and said data and information about the living human or animal.

7. The method of claim 1, wherein following said correlating, at least some elements of said processed data and information of said acquired living human or animal anatomical feature hyper-spectral imaging data and information, said acquired living human or animal consumable object hyper-spectral imaging data and information, and said data and information about the living human or animal, are fed back to said generating and maintaining, to update or/and modify said generating and maintaining said living human- or animal-specific database containing data and information about the living human or animal.

8. The method of claim 1, wherein following said correlating, at least some elements of said generated living human or animal life quality data and information characteristic of at least one aspect of life quality of the living human or animal are fed back to said processing, to update or/and modify said processing of said acquired living human or animal anatomical feature hyper-spectral imaging data and information, said acquired living human or animal consumable object hyper-spectral imaging data and information, and said data and information about the living human or animal.

9. The method of claim 1, further comprising using said living human or animal life quality data and information characteristic of at least one aspect of life quality of the living human or animal to assist in managing life quality of the living human or animal.

10. The method of claim 1, wherein said acquiring, said generating and maintaining, said processing, and said using, are performed for each living human or animal of a plurality of living humans or animals, to thereby generate a first level or layer database comprising living human or animal life quality data and information characteristic of at least one aspect of life quality of said each living human or animal of said plurality of living humans or animals.

11. The method of claim 10, further comprising processing and analyzing said first level or layer database, to identify and group together elements thereof having in common at least one attribute or characteristic of said living human or animal life quality data and information.

12. The method of claim 11, wherein said attribute or characteristic comprises one of demographic type data and information and consumer type data and information of said plurality of living humans or animals, wherein said at least one common attribute or characteristics is associated with common one of demographic type data and information and consumer type data and information among said plurality of living humans or animals.

13. The method of claim 12, wherein said demographic type data and information is selected from the group consisting of home living places of said living humans or animals, work places of said living humans or animals, travel places of said living humans or animals, hobbies of said living humans or animals, sexes of said living humans or animals, ages of said living humans or animals, weights of said living humans or animals, heights of said living humans or animals, skin colors of said living humans or animals, eye colors of said living humans or animals, hair colors of said living humans or animals, and anatomical features of said living humans or animals.

14. The method of claim 12, wherein said consumer type data and information is selected from the group consisting of substances consumable by said living humans or animals.

15. The method of claim 14, wherein said substances consumable by said living humans or animals are selected from the group consisting of foods and food products, water and water products, air, clothing, bedding, toiletries and bathroom products, cosmetics and cosmetic products, pharmaceuticals and pharmaceutical products, and, medicines and medicine or medicinal products.

16. The method of claim 11, further comprising generating a second level or layer database comprising a plurality of groups, wherein each said group is identifiable according to said at least one common attribute or characteristic of said living human or animal life quality data and information.

17. The method of claim 16, further comprising processing and analyzing said second level or layer database of said plurality of groups, for characterizing living human or animal life quality data and information of said plurality of living humans or animals.

18. The method of claim 17, wherein said processing and analyzing said second level or layer database includes cross referencing and correlating elements of said second level or layer database containing data and information of said plurality of groups.

19. The method of claim 17, further comprising generating a third level or layer database comprising living human or animal life quality data and information characteristic of said plurality of living humans or animals.

20. The method of claim 19, further comprising processing and analyzing, and using, said third level or layer database for making predictions about said living human or animal life quality data and information of said plurality of living humans or animals.

21. The method of claim 20, further comprising using said predictions to assist in managing life quality of one or more of said each living human or animal of said plurality of living humans or animals.

22. The method of claim 1, wherein said acquiring hyper-spectral imaging data and information of: said at least one anatomical feature of the living human or animal, and said at least one substance consumable by the living human or animal is performed by a hyper-spectral imaging unit.

23. The method of claim 22, wherein a controller-processor is configured to control said hyper-spectral imaging unit, wherein said controller-processor is operatively connected to said hyper-spectral imaging unit and to said data-information processing unit.

24. The method of claim 22, wherein further comprising a controller-processor configured to control said hyper-spectral imaging unit, wherein data and information, or/and control signals, are transferrable one of between said controller-processor and said hyper-spectral imaging unit and between said data-information processing unit and said controller-processor.

* * * * *